United States Patent [19]

Hendrickx et al.

[11] 3,966,741

[45] June 29, 1976

[54] PROCESS FOR THE PREPARATION OF SUBSTITUTED OR UNSUBSTITUTED 4-PYRIDYLTHIOACETIC ACID

[75] Inventors: Andreas J. J. Hendrickx, Venlo; Willem H. van Duyl, Grubbenvorst, both of Netherlands

[73] Assignee: Océ-Andeno B.V., Venlo, Netherlands

[22] Filed: Dec. 4, 1974

[21] Appl. No.: 529,457

[30] Foreign Application Priority Data
Dec. 13, 1973 Netherlands............. 7317069

[52] U.S. Cl. ........................................ 260/294.8 G
[51] Int. Cl.² ........................................ C07D 213/70
[58] Field of Search ............................. 260/294.8 G

[56] References Cited
UNITED STATES PATENTS
3,644,377  2/1972  Sapino, Jr. et al.......... 260/294.8 G OTHER PUBLICATIONS
Okamoto et al., Chem. Pharm. Bulletin (Tokyo) vol. 11, (1963), pp. 785–792.

Katritsky et al., J. Chem. Soc. (1958) pp. 1263–1266.
Werner, Industrial and Engineering Chem., vol. 40, No. 9, (1948), pp. 1574–1581.

Primary Examiner—Henry R. Siles
Assistant Examiner—Bernard Dentz
Attorney, Agent, or Firm—Albert C. Johnston

[57] ABSTRACT

4-Pyridylthioacetic acid is prepared economically without the formation of any noxious substance by (1) reacting a 4-nitropyridyl-N-oxide with a lower alkyl thioglycolate or with thioglycolic acid to form 4-thioglycolic acid (or 4-thioglycolate)-pyridyl-N-oxide, (2) reducing the latter oxide in the form of its 4-alkyl thioglycolate to obtain the corresponding 4-pyridylthioglycolic acid ester, and (3) converting said ester into a 4-pyridylthioacetic acid by saponification followed by acidification. When a lower alkyl thioglycolate is used for the reaction in step (1), step (2) can follow directly for reduction of the reaction product, and high yields are obtained.

14 Claims, No Drawings

PROCESS FOR THE PREPARATION OF SUBSTITUTED OR UNSUBSTITUTED 4-PYRIDYLTHIOACETIC ACID

This invention relates to a process for the preparation of a substituted or unsubstituted 4-pyridylthioacetic acid from a 4-nitropyridine-N-oxide compound.

4-Pyridylthioacetic acid is important as an intermediate product for the preparation of biologically active cephalosporins. Although various processes for the preparation of 4-pyridylthioacetic acid are known, extensive efforts have been made in order to find a new process which would be simpler and/or more economical than the processes already known.

A known process for the preparation of 4-pyridylthioacetic acid is, for instance, the process based on 4-(1-pyridyl)pyridinium-chloride-hydrochloride. Dutch patent application No. 71 04 539, heretofore laid open for public inspection, describes the preparation of 4-pyridylthioacetic acid from 4-(1-pyridyl)pyridinium-chloride-hydrochloride by treating the latter with mercapto-acetic acid (=thioglycolic acid) in water at a pH of about 7.

In Chem. Ber. 89 2921–33 (1956) the conversion of 4-(1-pyridyl)-pyridiniumchloride-hydrochloride into the ethyl-4-pyridylthio-acetate by means of $H_2S$ and $ClCH_2COOEt$ is mentioned, which reaction was successful with a yield of only 26%. The subsequent hydrolysis to 4-pyridylthioacetic acid brought about a yield of 46%, so that the total yield of this two-step preparation of 4-pyridylthioacetic acid amounted to only 12%.

German patent specification 1 225 178 describes the preparation of 4-pyridylthioacetic acid from 1-(4-pyridyl)pyridiniumchloride-hydrochloride by treating this compound with $BrCH_2CO_2H$ and $H_2S$.

It is also known to use 4- or γ-mercaptopyridine as the starting compound. For instance, in J. Chem. Soc. 1939 873–877, King and Ware described the preparation of 4-pyridylthioacetic acid by treating 4-mercaptopyridine with $ClCH_2COOH$ in a weakly basic medium, while Takahashi et al, as described in Pharm. Bull. (Japan) 2 30–34 (1954), obtain methyl-4-pyridylthioacetate by heating 4-mercaptopyridine for one hour on a water-bath with $ClCH_2CO_2Me$. In Gazz. Chim. Ital. 84 584–594 (1954), Musante and Fabbrini mention the preparation of 4-pyridylthioacetic acid by causing 4-mercapto-pyridine to react with $ClCH_2CONEt_2$ and treating the resulting 4-(diethylcarbamoylmethylmercapto)pyridine with KOH. In Wiss. Z. Tech. Hochsch. Chem. Leuna-Merseburg 2 187–193 (1959–1960) the preparation of (2-methyl-4-pyridylthio)acetic acid from $ClCH_2CO_2H$ and 4-mercapto-2-methylpyridine is mentioned, the latter product being obtained by converting 4-nitro-2-methylpyridine-N-oxide into 4-chloro-2-methyl-pyridine and causing this to react with KHS.

The preparation processes based on 4-(1-pyridyl)pyridinium-chloride-hydrochloride all have the disadvantage that, per kilogram of 4-pyridylthioacetic acid, about half a kilogram of pyridine which is noxious to the environment, is released. Moreover the yield varies: Once it is high (70–95%), as mentioned in said Dutch application No. 71 04 539, then it is low (12%), as appears from Chem. Ber. 89 2921–33 (1956).

The object of the present invention is to provide a process for the preparation of 4-pyridylthioacetic acid whereby, while maintaining the high yields of about 80% such as mentioned in the above-mentioned Dutch patent application, there is no production of secondary products or waste products that are noxious to the environment. Further, the invention makes it possible to start from a cheaper starting substance, thus providing an economically more attractive process for the preparation of 4-pyridylthioacetic acid.

According to the present invention, substituted or unsubstituted 4-pyridylthioacetic acid is prepared from a 4-nitropyridine-N-oxide compound by a process in which (1) a 4-nitropyridine-N-oxide according to the formula I below,

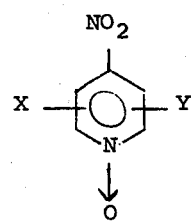

is converted by reaction with a compound having the formula $HSCH_2CO_2R$ into a compound according to formula II below,

II.

(2) then the formula II compound, either as such if its moiety R is an alkyl group or after esterification if R is a hydrogen atom, is reduced into a compound according to formula III below,

III.

and (3) then the formula III compound is converted by saponification and subsequent acidification into a 4-pyridylthioacetic acid having the formula IV below,

IV.

In these formulae X represents a hydrogen atom, a halogen atom or a $C_{1-4}$ alkyl or alkoxy group, Y represents a hydrogen atom or a $C_{1-4}$ alkyl or alkoxy group and R stands for a hydrogen atom or a $C_{1-4}$ alkyl group, with the understanding that the reduction always takes place with a compound according to formula II in which R stands for a $C_{1-4}$ alkyl group.

As compared with the preparation process based on 1-(4-pyridyl)-pyridiniumchloride-hydrochloride, the process according to the invention has the advantage that it is more economical and produces no pyridine, which is noxious to the environment, as a waste product. Moreover the yield of the process according to the invention is often considerably higher than the yield of the known preparation process based on 1-(4-pyridyl)-pyridinium-chloride.HCl, for instance as described in Chem. Ber. 89 2921–33 (1956).

Compared with the preparation process based on 4- or γ-mercaptopyridine, the process according to the invention has the advantage that 4-nitropyridine-N-oxide is a cheaper starting substance than the 4- or Γ-mercaptopyridine, so that the process according to the invention is less expensive.

Compared with the above-mentioned prior art process for the preparation of (2-methyl-4-pyridylthio)-acetic acid from a 4-nitropyridine-N-oxide compound, the process according to the invention has the advantage that one step less is sufficient for the reaction. In the known process the nitro group in the 4-nitropyridine-N-oxide compound is first replaced by a chlorine atom by reaction with HCl, after which the chlorine atom is replaced by a 4-mercapto group by reaction with KHS, after which the $S-CH_2CO_2H$ group is formed at the 4-position by reaction with $ClCH_2CO_2H$. In the process according to the invention the conversion of the nitro group into the group $S-CH_2CO_2R$ takes place in one step, which of course is a great advantage.

When the compound of formula $HSCH_2CO_2R$ as used in the first step of the present process, i.e., in the reaction converting the compound of formula I into that of formula II, is an ester of thioglycolic acid, i.e., is one in which R is an alkyl group rather than a hydrogen atom, advantages are obtained not only in that the yield is higher but also in that the reduction in step (2) of the process can be carried out successively, i.e. directly following the reaction of step (1). In those cases where R represents a hydrogen atom, the acid group must first be esterified before reduction can be carried out, which consequently involves an extra reaction step. Preferably the methyl ester or ethyl ester of $HSCH_2COOH$ is used for the first step.

It has been found advantageous to carry out the conversion of the compound of formula I into that of formula II in an alcohol medium in the presence of a base and at a temperature between 0° and 50°C. Solvents which may be used include methanol, ethanol and isopropanol, or mixtures of these, any of which may be diluted with water if so desired. Preferably a medium containing water and 80–90% of alcohol is used, although alcohol percentages from 50% up are useful. The base used can be, for instance, the hydroxide or carbonate of sodium or potassium or any of various tertiary amines. Preferably triethylamine is used.

Although the reaction temperature can be moderate and can vary, for instance, from 0° to 50°C, preferably a temperature between 30° and 35°C is employed.

It has further been found that the reduction of the compound of formula II into that of formula III can be effected advantageously by means of a so-called Béchamp-reduction, i.e., by the action of iron in the presence of a catalytic quantity of hydrochloric acid or acetic acid.

A special advantage of the process according to preferred embodiments of the invention is that, when the first reaction step is carried out with an ester of thioglycolic acid, the reduction step (2) can be carried out successively, i.e., without preceding isolation of the formed ester of the 4-pyridylthioglycolic acid-N-oxide.

Upon the end of the reduction the iron paste is filtered off, and the filtrate containing the compound according to formula III is treated with an alkali hydroxide, e.g., sodium hydroxide, and is heated until the saponification is complete. The compound according to formula IV is then obtained by acidification of the reaction mixture to a pH of 3 to 4, filtering off the precipitated acid and drying this precipitate.

Although a substituent X may occupy the 2- or the 3-position and a substituent Y the 5- or 6-position, when substituents X and Y are present they preferably occupy the positions in ortho relation to the pyridyl-nitrogen atom. Any of the 2-, 3-, 5- and 6-ring positions that is not occupied by a substituent rather than hydrogen is of course occupied by a hydrogen atom. When substituted, the presence of only a single substituent in a position ortho to the pyridyl-nitrogen atom is preferred. Preferably X represents a hydrogen or halogen atom and Y represents a hydrogen atom. Among the components of formula I particularly suitable for the process are, for instance, those having unsubstituted pyridyl-nuclei and those having 2-methyl-, 2-chloro- and 2-bromo-substituted pyridyl-nuclei.

The following examples serve to illustrate the invention.

EXAMPLE 1

A mixture of 400 ml of ethanol, 40 ml of water, 117 g (= 1.1 moles) of methyl thioglycolate, 140 g (= 1.0 mole) of 4-nitropyridine-N-oxide and 112 g (= 1.1 moles) of triethylamine was stirred for 1–2 hours at 30°–35°C.

After the reaction had ended, 105 ml of hydrochloric acid (specific gravity 1.152) were added to the reaction mixture while stirring, after which while stirring the whole was dosed into a refluxing boiling mixture of 250 ml of ethanol, 50 ml of water, 336 g of iron powder and 10 ml of hydrochloric acid (specific gravity 1.152). When the reduction was complete, the iron paste while still warm was filtered off and washed with ethanol.

After 100 g of NaOH was stirred into the filtrate, the mixture was heated up to reflux and 300 ml was distilled away. This distillate contained about 80 g of triethylamine which could be used anew.

To the residue 150 ml of water was added and the whole was filtered over 10 g of carbon. By the addition of 150 ml of hydrochloric acid (specific gravity 1.152) to the filtrate a pH value of 3–4 was obtained. After cooling of the acidified filtrate, light-brown crystals existed which were filtered off and purified. The yield of colorless fine crystals of the 4-pyridylthioacetic acid, melting point 268°–270°C (decomp.), amounted to 135 g (=80%).

When using the ethyl ester of thioglycollic acid instead of the methyl ester in the process according to this example, the result was the same; also, the yield of purified 4-pyridylthioacetic acid was again about 80%.

EXAMPLE 2

A mixture of 100 ml of methanol, 12.5 ml of water, 29.3g(= 0.275 mole) of methyl thioglycolate, 35.4 g (= 0.25 mole) of 4-nitropyridine-N-oxide and 28 g (=

0.275 mole) of triethylamine was stirred for 2 hours at a temperature of 30°–35°C.

After the mixture had been dried by evaporating the solvent at decreased pressure, toluene was added, and once more the mixture was dried by evaporation. The residue was recrystallized from 800 ml of ethylacetate.

The methyl ester of the 4-pyridylthioacetic acid-N-oxide was thus obtained in a yield of 34 g (= 68%), consisting of whitish yellow crystals of melting point 112°C. From the mother liquor still another 11.1 g (=22%) of this methyl ester was isolated, so that the total yield amounted to 90%.

The same reaction carried out with thioglycolic acid itself gave a yield of only 59% of 4-pyridylthioacetic acid-N-oxide, which yield contrasts unfavorably with the yield of 90% obtained when using the methyl- or ethyl ester of thioglycolic acid.

The above prepared methyl 4-pyridylthioacetate-N-oxide could be reduced immediately, while the 4-pyridylthioacetic acid-N-oxide had first to be esterified before the reduction step could be carried out. Accordingly, it is advantageous to use the methyl- or ethyl ester of thioglycolic acid in preference to the thioglycolic acid itself.

We claim:

1. A process for the preparation of substituted or unsubstituted 4-pyridylthioacetic acid, which comprises (1) reacting a 4-nitro-pyridine-N-oxide having the formula

I

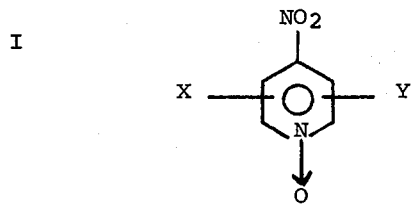

with a compound having the formula $HSCH_2CO_2R$ to form a compound having the formula

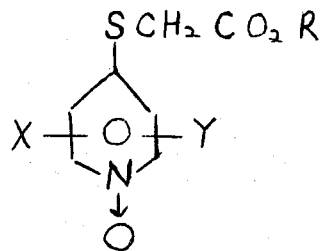

in which formula X is a hydrogen or a halogen atom or an alkyl or alkoxy group, said groups containing 1–4 carbon atoms, Y is a hydrogen atom, an alkyl or alkoxy group, said groups containing 1–4 carbon atoms and R is an alkyl group containing 1–4 carbon atoms; (2) reducing the formed compound by reacting it with finely divided iron in the presence of a catalytic quantity of hydrochloric acid or acetic acid to obtain a corresponding 4-pyridylthioacetic acid ester, and (3) converting said ester into the corresponding 4-pyridylthioacetic acid by saponification followed by acidification.

2. A process according to claim 1 in which R is a methyl or ethyl group.

3. A process according to claim 1, said reacting of said 4-nitropyridine-N-oxide being effected in an alcohol medium in the presence of a base and at a temperature between 0° and 50°C.

4. A process according to claim 3, said medium containing water and about 80 to 90% of an alcohol selected from the group consisting of methanol, ethanol, isopropanol and mixtures thereof.

5. A process according to claim 3, said base being triethylamine.

6. A process according to claim 3, said temperature being between 30° and 35°C.

7. A process according to claim 1, said reacting of said 4-nitropyridine-N-oxide being effected in a medium containing water and about 80 to 90% of an alcohol selected from the group consisting of methanol, ethanol, isopropanol and mixtures thereof, in the presence of triethylamine and at a temperature of about 30° to 35°C.

8. A process according to claim 1, wherein said reducing is effected without preceding isolation of the formed 4-thioglycolate-pyridyl-N-oxide from the product of reaction (1).

9. A process according to claim 1, in which each of X and Y occupies a ring position ortho to the pyridyl-nitrogen atom.

10. A process according to claim 1, in which said 4-nitro-pyridine-N-oxide is unsubstituted, X and Y each being a hydrogen atom.

11. A process according to claim 1, in which one of X and Y is a hydrogen atom and the other is a halogen atom at a ring position ortho to the pyridyl-nitrogen atom.

12. A process according to claim 1, in which one of X and Y is a hydrogen atom and the other is a methyl group at a ring position ortho to the pyridyl-nitrogen atom.

13. A process for the preparation of 4-pyridylthioacetic acid, which comprises (1) reacting 4-nitro-pyridine-N-oxide with methyl thioglycolate or ethyl thioglycolate in a medium containing water and about 80 to 90% of an alcohol selected from the group consisting of methanol, ethanol, isopropanol and mixtures thereof, in the presence of a base and at a temperature of about 30° to 35°C., thereby forming a 4-thioglycolate-pyridyl-N-oxide; (2) reducing the latter oxide by reacting it with finely divided iron in the presence of a catalytic quantity of hydrochloric acid or acetic acid, thus forming the corresponding 4-thioglycolate-pyridine; and (3) saponifying the last-mentioned compound with alkali and thereafter acidifying it to convert it into 4-pyridylthioacetic acid.

14. A process according to claim 13, said base being triethylamine.

* * * * *